(12) United States Patent
Fangrow, Jr.

(10) Patent No.: US 7,931,627 B2
(45) Date of Patent: Apr. 26, 2011

(54) CHECK VALVE FOR MEDICAL Y-SITE

(75) Inventor: Thomas F. Fangrow, Jr., Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 1304 days.

(21) Appl. No.: 11/415,995

(22) Filed: May 2, 2006

(65) Prior Publication Data

US 2006/0264853 A1 Nov. 23, 2006

Related U.S. Application Data

(63) Continuation of application No. 11/048,399, filed on Feb. 1, 2005, now Pat. No. 7,670,322.

(51) Int. Cl.
*A61M 5/00* (2006.01)
*A61M 25/00* (2006.01)
*F16L 37/28* (2006.01)
*F16K 15/16* (2006.01)

(52) U.S. Cl. ............ 604/247; 604/284; 251/149.1; 137/855

(58) Field of Classification Search ........... 604/6.1, 604/9, 32–34, 99.03, 99.04, 167.03, 236, 604/237, 246–249, 256, 264, 280, 284, 288.03, 604/523; 251/149.1; 137/855, 895, 112
See application file for complete search history.

(56) References Cited

U.S. PATENT DOCUMENTS

| | | |
|---|---|---|
| 1,578,517 A | 3/1926 | Hein |
| 2,999,499 A | 9/1961 | Willet |
| 3,416,567 A | 12/1968 | Von Dardel et al. |
| 3,502,097 A | 3/1970 | Mueller |
| 3,572,375 A | 3/1971 | Rosenberg |
| 3,797,486 A | 3/1974 | Shaps |
| 3,807,444 A | 4/1974 | Fortune |
| 3,830,241 A | 8/1974 | Dye et al. |
| 3,852,385 A | 12/1974 | Huggins |
| 3,965,910 A | 6/1976 | Fischer |
| 3,994,293 A | 11/1976 | Ferro |

(Continued)

FOREIGN PATENT DOCUMENTS

EP 0 370 997 5/1990

(Continued)

OTHER PUBLICATIONS

Engineering drawings for ICU Medical Inc.'s 1o2® Valve.

(Continued)

*Primary Examiner* — Nicholas D Lucchesi
*Assistant Examiner* — Victoria P Campbell
(74) *Attorney, Agent, or Firm* — Knobbe Martens Olson & Bear LLP

(57) ABSTRACT

A check valve for use in a Y-site in an infusion system comprises a fixation portion configured to retain the check valve in a common lumen of the Y-site, and a flap member extending axially from the fixation portion. The flap member has an outer surface, at least a portion of which is configured to engage an internal wall of the common lumen overlying an inlet from a main lumen. In one embodiment, the flap member comprises a pocket, which surrounds surrounding the hole and any burr extending from the wall adjacent the hole. In some embodiments, the flap member is resiliently biased towards a sealed position, and can flex to allow fluid flow from the main lumen to the common lumen.

9 Claims, 14 Drawing Sheets

U.S. PATENT DOCUMENTS

| | | | |
|---|---|---|---|
| 4,005,710 A | 2/1977 | Zeddies et al. | |
| 4,063,555 A | 12/1977 | Ulinder | |
| 4,079,738 A | 3/1978 | Dunn et al. | |
| 4,121,585 A | 10/1978 | Becker, Jr. | |
| 4,149,535 A | 4/1979 | Volder | |
| 4,191,183 A | 3/1980 | Mendelson | |
| 4,219,912 A | 9/1980 | Adams | |
| 4,257,416 A | 3/1981 | Prager | |
| 4,294,249 A | 10/1981 | Sheehan et al. | |
| 4,338,933 A | 7/1982 | Bayard et al. | |
| 4,392,851 A | 7/1983 | Elias | |
| 4,411,662 A | 10/1983 | Pearson | |
| 4,447,230 A | 5/1984 | Gula et al. | |
| 4,573,974 A | 3/1986 | Ruschke | |
| 4,666,429 A | 5/1987 | Stone | |
| 4,730,635 A | 3/1988 | Linden | |
| 4,735,607 A | 4/1988 | Keith, Jr. | |
| 4,781,702 A | 11/1988 | Herrli | |
| 4,790,832 A | 12/1988 | Lopez | |
| 4,817,825 A | 4/1989 | Freese | |
| 4,819,684 A | 4/1989 | Zaugg et al. | |
| 4,834,716 A | 5/1989 | Ogle, II | |
| 4,842,591 A | 6/1989 | Luther | |
| 4,850,978 A | 7/1989 | Dudar et al. | |
| 4,874,369 A | 10/1989 | Kulle et al. | |
| 4,878,897 A | 11/1989 | Katzin | |
| 4,889,527 A | 12/1989 | Herrli | |
| 4,911,705 A | 3/1990 | Heinzerling et al. | |
| 4,915,687 A | 4/1990 | Sivert | |
| 4,929,235 A | 5/1990 | Merry et al. | |
| 4,932,944 A | 6/1990 | Jagger | |
| 4,946,445 A | 8/1990 | Lynn | |
| 4,964,855 A | 10/1990 | Todd et al. | |
| 4,981,469 A | 1/1991 | Whitehouse et al. | |
| 4,998,713 A | 3/1991 | Vaillancourt | |
| 4,998,921 A | 3/1991 | Vickroy et al. | |
| 4,998,927 A | 3/1991 | Vaillancourt | |
| 5,049,128 A | 9/1991 | Duquette | |
| 5,080,652 A | 1/1992 | Sancoff et al. | |
| 5,098,405 A | 3/1992 | Peterson et al. | |
| 5,100,394 A | 3/1992 | Dudar et al. | |
| 5,100,395 A | 3/1992 | Rosenberg | |
| 5,112,301 A | 5/1992 | Fenton et al. | |
| 5,113,911 A | 5/1992 | Hirsh | |
| 5,122,123 A | 6/1992 | Vaillancourt | |
| 5,135,489 A | 8/1992 | Jepson et al. | |
| 5,147,333 A | 9/1992 | Raines | |
| 5,158,554 A | 10/1992 | Jepson et al. | |
| 5,163,922 A | 11/1992 | McElveen, Jr. et al. | |
| 5,167,642 A | 12/1992 | Fowles | |
| 5,167,647 A | 12/1992 | Wijkamp et al. | |
| 5,167,648 A | 12/1992 | Jepson et al. | |
| 5,171,234 A | 12/1992 | Jepson et al. | |
| 5,188,620 A | 2/1993 | Jepson et al. | |
| 5,195,992 A | 3/1993 | Dudar et al. | |
| 5,201,717 A | 4/1993 | Wyatt et al. | |
| 5,203,775 A | 4/1993 | Frank et al. | |
| 5,211,638 A | 5/1993 | Dudar et al. | |
| 5,221,271 A | 6/1993 | Nicholson et al. | |
| 5,242,432 A | 9/1993 | DeFrank | |
| 5,255,676 A | 10/1993 | Russo | |
| 5,273,533 A | 12/1993 | Bonaldo | |
| 5,281,206 A | 1/1994 | Lopez | |
| 5,290,222 A | 3/1994 | Feng et al. | |
| 5,306,265 A | 4/1994 | Ragazzi | |
| 5,330,450 A | 7/1994 | Lopez | |
| 5,342,316 A | 8/1994 | Wallace | |
| 5,342,326 A | 8/1994 | Peppel et al. | |
| 5,348,542 A | 9/1994 | Ellis | |
| 5,356,396 A | 10/1994 | Wyatt et al. | |
| 5,370,624 A | 12/1994 | Edwards et al. | |
| 5,385,547 A | 1/1995 | Wong et al. | |
| 5,395,348 A | 3/1995 | Ryan | |
| 5,401,245 A | 3/1995 | Haining | |
| 5,407,437 A | 4/1995 | Heimreid | |
| 5,439,451 A | 8/1995 | Collinson et al. | |
| 5,445,630 A | 8/1995 | Richmond | |
| 5,470,319 A | 11/1995 | Mayer | |
| 5,549,577 A | 8/1996 | Siegel et al. | |
| 5,578,016 A | 11/1996 | Zinger | |
| 5,603,706 A | 2/1997 | Wyatt et al. | |
| 5,613,663 A | 3/1997 | Schmidt et al. | |
| 5,660,205 A | 8/1997 | Epstein | |
| 5,676,346 A | 10/1997 | Leinsing | |
| 5,700,248 A | 12/1997 | Lopez | |
| 5,738,663 A | 4/1998 | Lopez | |
| 5,749,861 A | 5/1998 | Guala et al. | |
| RE35,841 E | 7/1998 | Frank et al. | |
| 5,782,816 A | 7/1998 | Werschmidt et al. | |
| 5,788,215 A | 8/1998 | Ryan | |
| 5,810,768 A | 9/1998 | Lopez | |
| 5,810,792 A | 9/1998 | Fangrow et al. | |
| 5,839,715 A | 11/1998 | Leinsing | |
| 5,901,942 A | 5/1999 | Lopez | |
| 5,957,898 A | 9/1999 | Jepson et al. | |
| 5,971,950 A | 10/1999 | Lopez et al. | |
| 6,019,748 A | 2/2000 | Lopez | |
| 6,063,062 A | 5/2000 | Paradis | |
| 6,068,617 A | 5/2000 | Richmond | |
| 6,117,114 A | 9/2000 | Paradis | |
| 6,142,446 A | 11/2000 | Leinsing | |
| 6,171,287 B1 | 1/2001 | Lynn et al. | |
| 6,197,005 B1 | 3/2001 | Gerlach et al. | |
| 6,245,048 B1 | 6/2001 | Fangrow et al. | |
| 6,261,282 B1 | 7/2001 | Jepson et al. | |
| 6,269,704 B1 | 8/2001 | Ziv et al. | |
| 6,344,033 B1 | 2/2002 | Jepson et al. | |
| 6,364,861 B1 | 4/2002 | Feith et al. | |
| 6,428,520 B1 | 8/2002 | Lopez et al. | |
| 6,485,472 B1 | 11/2002 | Richmond | |
| 6,491,668 B1 | 12/2002 | Paradis | |
| 6,511,434 B1 | 1/2003 | Haytman et al. | |
| 6,589,197 B1 | 7/2003 | Doi et al. | |
| 6,599,273 B1 | 7/2003 | Lopez | |
| 6,695,817 B1 | 2/2004 | Fangrow | |
| 6,827,709 B2 | 12/2004 | Fujii | |
| 6,871,838 B2 | 3/2005 | Raines et al. | |
| 7,033,339 B1 | 4/2006 | Lynn | |
| 2003/0095883 A1 | 5/2003 | Hauser | |
| 2004/0006330 A1 | 1/2004 | Fangrow | |
| 2004/0049169 A1* | 3/2004 | Fischell | 604/537 |
| 2004/0210162 A1 | 10/2004 | Wyatt et al. | |
| 2005/0038413 A1 | 2/2005 | Sansoucy | |
| 2005/0256461 A1 | 11/2005 | DiFiore et al. | |
| 2005/0256500 A1 | 11/2005 | Fujii | |
| 2005/0267417 A1 | 11/2005 | Secrest et al. | |
| 2006/0089603 A1 | 4/2006 | Truitt et al. | |
| 2006/0155213 A1 | 7/2006 | Madonia | |
| 2006/0163515 A1 | 7/2006 | Ruschke | |

FOREIGN PATENT DOCUMENTS

| | | |
|---|---|---|
| EP | 0 438 909 | 10/1994 |
| GB | 2001146 A | 1/1979 |
| NL | 8801496 A | 1/1990 |
| WO | WO 2004/098689 A1 | 11/2004 |
| WO | PCT/US2005/046441 | 4/2006 |

OTHER PUBLICATIONS

Brochure for "Marvelous" Connector by Elcam Medical.
Raisch et al., Evaluation of Piggyback Administration Sets, Dec. 1977.
*Nursing Photobook: Managing I.V. Therapy*, Published 1983 by Springhouse Corp. of Springhouse, Pennsylvania.
*Manual for I.V. Therapy Procedures* (2d ed. 1985) by Shila R. Channell.
*102 Fluid Delivery System.*
U.S. Appl. No. 11/048,399, filed Feb. 1, 2005, pending.
U.S. Appl. No. 11/415,545, filed May 2, 2006, pending.
U.S. Appl. No. 11/417,289, filed May 2, 2006, pending.
U.S. Appl. No. 11/417,308, filed May 2, 2008, pending.
U.S. Appl. No. 11/415,939, filed May 2, 2006, pending.
U.S. Appl. No. 11/415,698, filed May 2, 2006, pending.

* cited by examiner

CHECK VALVE FOR MEDICAL Y-SITE

RELATED APPLICATION

This application is a continuation of U.S. patent application Ser. No. 11/048,399 filed Feb. 1, 2005, now U.S. Pat. No. 7,670,332 which is incorporated herein by reference.

DESCRIPTION OF THE RELATED ART

Intravenous delivery of fluids has become an important aspect of modern medicine. Infusion systems are used to deliver hydrating and nourishing fluids, antibiotics, anesthetics, and other medications to patients. Infusion systems typically include a bag of fluid joined to a fluid line which is connected to an IV needle or catheter inserted into a patient's blood vein, thereby allowing the fluid to be dripped from the bag and into the patient.

In many infusion systems, Y-sites are placed in the fluid line, between the fluid bag and the needle or catheter, to provide a second path through which other fluids or drugs can be injected into the infusion system. Standard Y-sites are so named because a fork is created between a main lumen having an input port for introducing infusion liquid and a secondary lumen with an injection port for injecting medication therethrough. The main lumen typically is configured to handle a constant or near-constant flow, and the secondary lumen is configured to handle an intermittent or periodic flow. The common lumen and the secondary lumen are typically coaxial, and thus the boundary between the common and secondary lumens is the region of confluence between the fluids flowing through the main and secondary lumens. An outlet in the Y-site is located at a distal end of the common lumen.

In some cases, the distally directed fluid flow in the common lumen is slower than a periodic burst of fluid introduced into the secondary lumen. This may create fluid pressure in the region where all three lumens are joined that is greater than the fluid pressure in the main lumen upstream of this juncture, causing a volume of fluid (e.g. medication) that has been injected through the secondary lumen to flow upwardly through the main lumen towards (and possibly into) an IV bag or another medical implement. This retrograde flow can dilute and delay delivery of the full dose of medication to the patient. While all of the medication may eventually reach the patient, it may not do so as quickly as might be desired.

SUMMARY

Therefore, it is desirable to provide a Y-site with a check-valve to prevent fluid from flowing from the secondary or common lumens into the main lumen of the Y-site, thereby insuring that fluids injected through the secondary lumen will be delivered to the patient as soon as possible.

Several embodiments of the present invention provide a check valve that reliably minimizes or prevents undesired backflow to a main lumen of a Y-site. In one embodiment, an infusion system comprises a combination of a check valve and a Y-site with a main lumen, a secondary lumen, and a common lumen. The check valve comprises a fixation portion engaging an internal wall of the secondary lumen. A flap member extends from the fixation portion along a portion of the internal wall. The flap member overlies a hole joining the lumens. The flap is resiliently biased toward a sealing position to cover the hole and prevent fluid flow in a direction from the common or secondary lumens into the main lumen, but is flexible to deflect and allow forward fluid flow from the main lumen into the common lumen. In some embodiments, the flap further comprises a pocket configured to surround the hole and any burr or flash that may be adjacent to the hole on the interior wall of the housing. In one such embodiment, a pocket is defined by a flange surrounding the flap member and sealing against the walls of the common and/or secondary lumens while holding a portion of the flap member away from the burr.

In another embodiment, a check valve comprises a fixation portion having a first end and a second end. The fixation portion has an outer dimension sized to retain the check valve in a lumen of a medical connector. A flap member extends axially from the second end of the fixation portion and has an attachment end joining the flap member to the fixation portion and a free end opposite the attachment end. The flap member can also comprise a curved outer surface, and a portion of the flap member is configured to engage an internal wall of a lumen of a medical connector. In one preferred embodiment, the check valve is configured to function within a medical connector with a circular inner lumen. In some embodiments, the flap member comprises a pocket surrounding the hole. In other embodiments, the pocket is defined by a flange extending outwards and surrounding the flap member.

A method of using a Y-site and check valve comprises preventing reverse flow directed from a common lumen to a main lumen of a medical Y-connector. The method comprises inserting a check valve having a fixation section and a resilient flap into a common or secondary lumen of a medical Y-site. The method further comprises securing the fixation section in the common and/or secondary lumens of the Y-site in a position that places the flap over an opening at the confluence of the main, secondary and common lumens.

BRIEF DESCRIPTION OF DRAWINGS

Having thus summarized the general nature of the invention, certain preferred embodiments and alternatives thereof will be described in detail with reference to the figures that follow, of which.

DETAILED DESCRIPTION

Figure 1A:
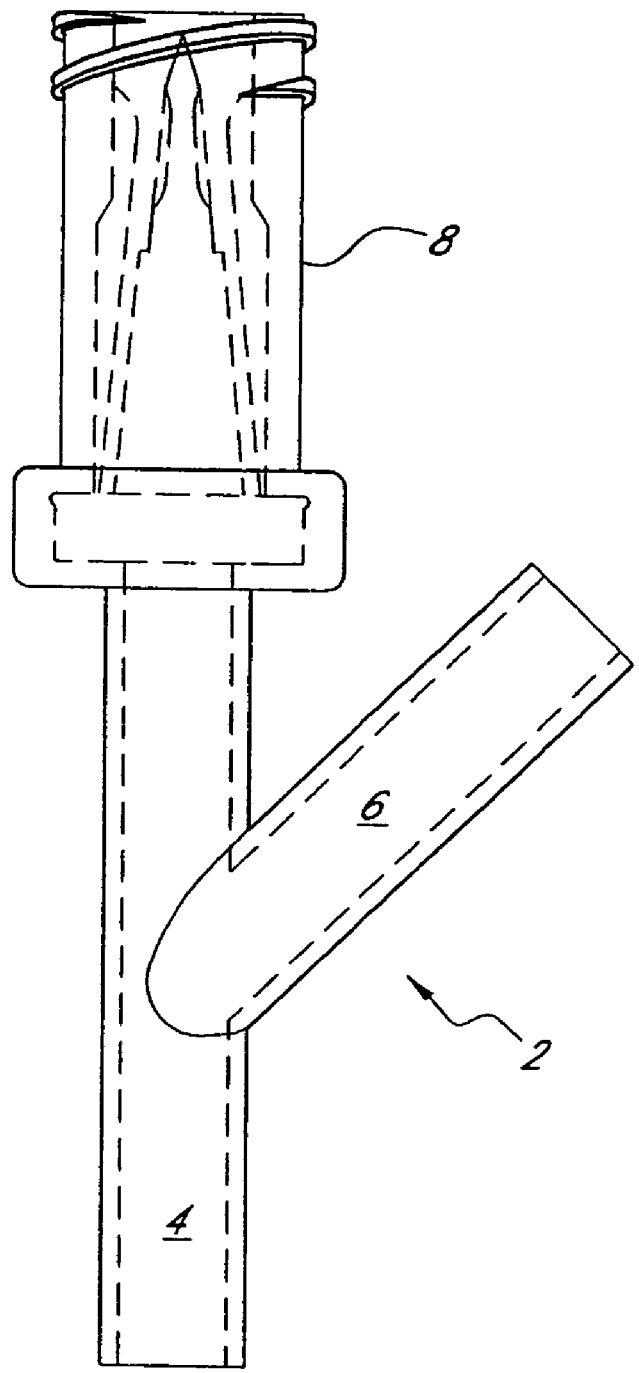
FIG. 1A is a perspective view of a medical Y-site with certain interior structures shown in phantom lining.

With reference to the attached figures, various embodiments of a Y-site check valve will now be described. FIG. 1A illustrates an example of a Y-site 2 with a needle-less connector 8 as illustrated and described in U.S. Pat. No. 6,599,273, incorporated herein by reference for all that it discloses. The illustrated needle-less connector 8 is a version of the CLAVE® needle-less connector sold by ICU Medical, Inc, San Clemente, Calif.

Figure 1B:
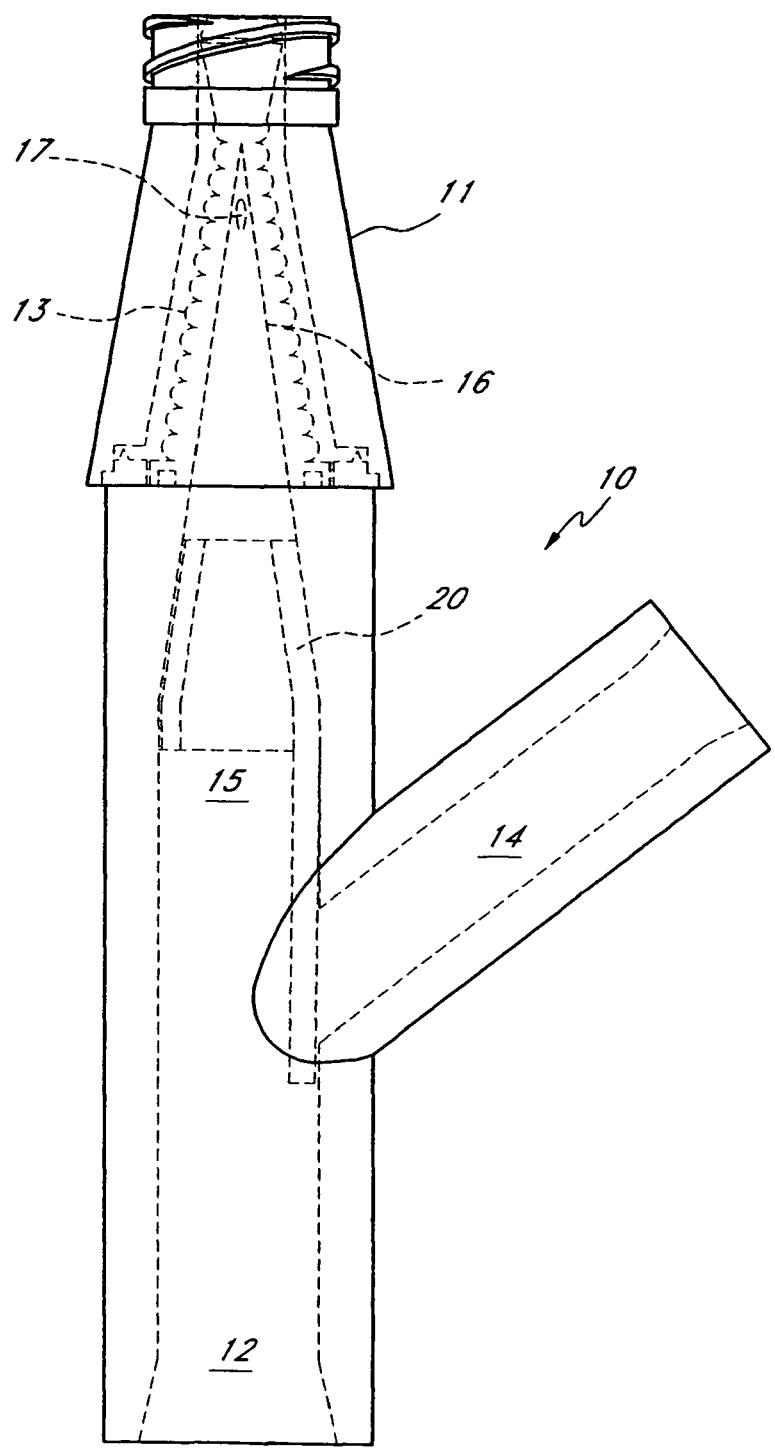
FIG. 1B is a perspective view of a Y-site with certain interior portions, including a check valve, shown in phantom lining.
Figure 1C:
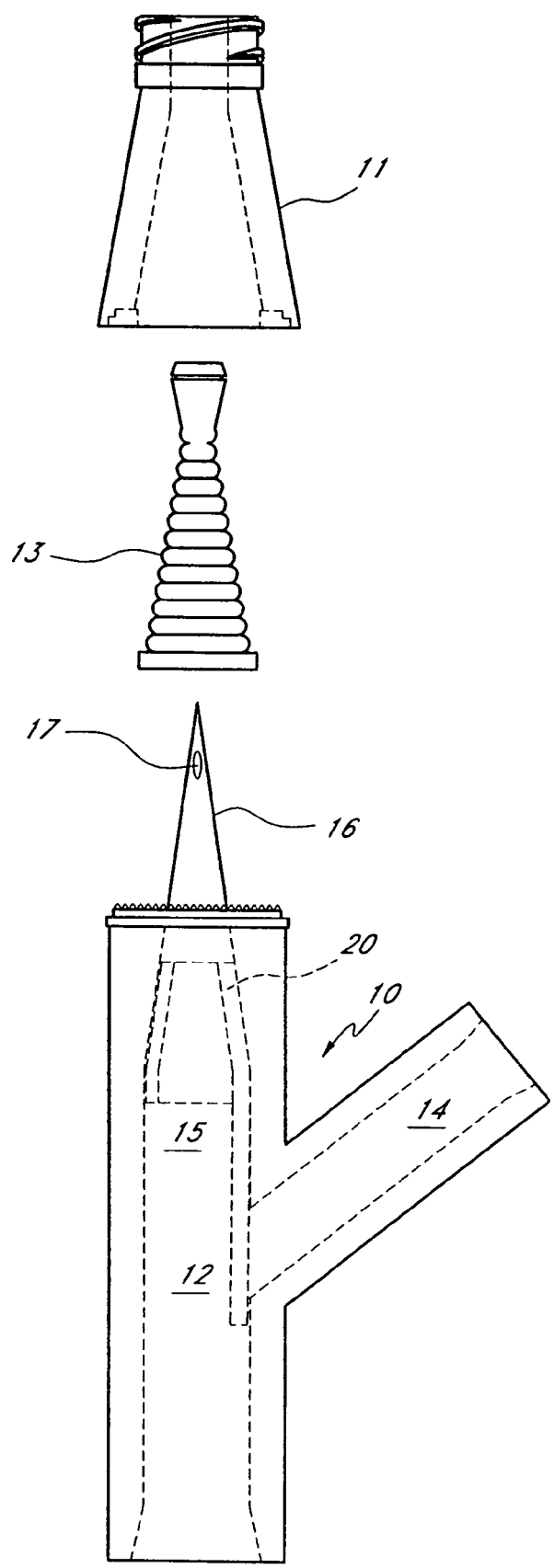
FIG. 1C is an exploded view of the Y-site with check valve of FIG. 1B.

FIG. 1B illustrates an embodiment of a Y-site 10 with a check valve 20 configured to prevent backflow from the common lumen 12 or secondary lumen 15 into the main drip lumen 14. In the illustrated embodiment, the Y-site 10 is attached to another version of the CLAVE® needle-less connector at its proximal end. The illustrated needle-less connector includes an outer housing 11, an inner seal element 13, and at tapered inlet port 16. Another medical implement, such as a syringe with a luer, can be inserted into the proximal opening of the connector to compress the seal element 13 in the distal direction. As the seal element 13 compresses, the tip of the inlet port 16 passes through the seal element 13. Fluid from the inserted medical implement is then forced into the proximal end of the connector. One or more holes 17 at or near the tip of the inlet port 16 allow the fluid to pass from the luer through the inlet port 16 and into the common lumen 12 of the Y-site. FIG. 1C shows the Y-site of FIG. 1B with the housing 11 and the seal element 13 of the connector detached from each other.

The illustrated needle-less connector is but one example of a connector that can be used to facilitate the attachment of the Y-site to another medical implement. Many other types of connectors, valves, and/or injection sites can be used, including connectors without an extended, tapered inlet port 16, and connectors that produce positive-flow, such as those illustrated and described in U.S. Pat. Nos. 6,245,048, 6,428,520, and 6,695,817, incorporated herein by reference for all that they disclose. In all of the embodiments described and illustrated herein, the connector at the proximal end can be formed as a unitary structure with the Y-site, or it can be formed separately and later attached to the Y-site by removable or non-removable means such as screw threads, snap rings, adhesives, or solvents. The Y-site can also be used without a connector in some applications.

Figure 2A:
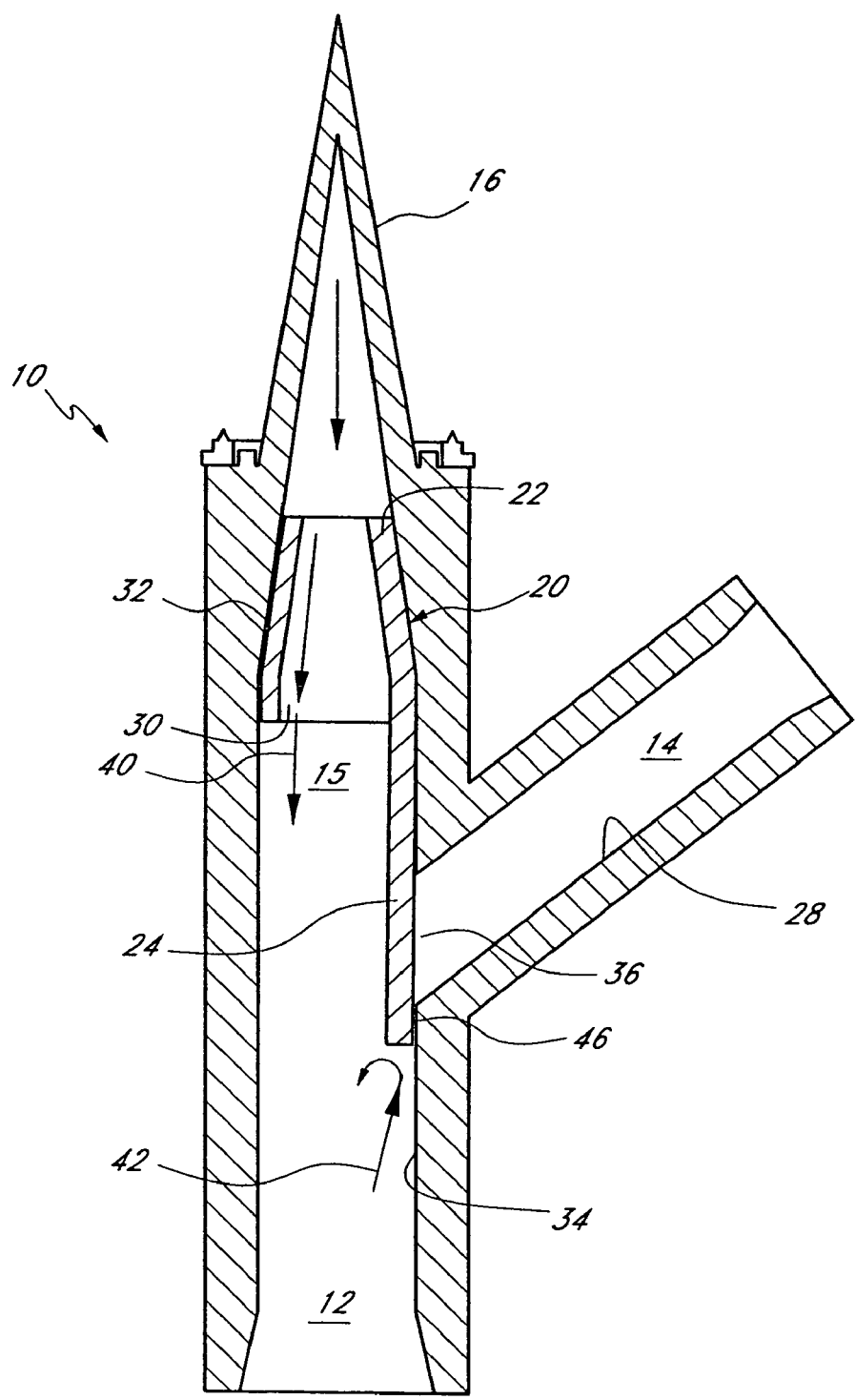
FIG. 2A is a schematic cross-sectional view of the Y-site of FIG. 1B with the check valve in a closed position, and the connector on the secondary lumen removed.

FIG. 2A illustrates the Y-site 10 of FIG. 1B with the housing 11 and the seal element 13 removed, thus exposing the tapered inlet port 16. The embodiments of the check valve 20 shown in FIG. 1B through FIG. 10 generally includes a fixation section 22 and a flap member 24 extending from the fixation section 22 to cover the opening at the intersection of the main lumen 14 with the common lumen 12. Embodiments of a check valve as described herein can have any length deemed appropriate for a particular Y-site. In some embodiments, the check valve 20 has an overall length $L_2$ of about 0.4" to about 0.8". One embodiment of a check valve has an overall length $L_2$ of about 0.6". The fixation section 22 is configured to secure the check valve 20 in a desired location within the common 12 or secondary 15 lumens of the Y-site.

In some embodiments, the fixation section 22 can have an internal lumen 30 extending axially therethrough, and can also comprise an outer wall 32 configured to engage an inner wall 34 of the common 12 or secondary 15 lumens of the Y-site 10. In some alternative embodiments, such as those shown in FIGS. 11-13, the fixation section comprises a protrusion, such as a prismatic body 90, configured to retain the check valve 20 in the Y-site common lumen 12 while allowing fluid flow around the protrusion.

FIG. 2A schematically illustrates a fluid 40 flowing through the common 12 and secondary 15 lumens of the Y-site, as well as through the lumen 30 of the check valve 20. The flap member 24 of the check valve 20 is shown preventing fluid 42 from flowing from the common lumen 12 into the main lumen 14. The flap member 24 is configured to seal or substantially seal against portions of the inner walls of the common 12 and secondary 15 lumens that surround the hole 36 joining the lumens 12, 14, 15. The cross-sections of the inner wall of the common 12 and secondary 15 lumens are generally circular. In such embodiments, the outer surface 46 of the flap member 24 can have a radius that is substantially the same as, or even slightly larger than, the radius of the inner wall 34 of the common lumen 12. In alternative embodiments, the inner wall 34 of the common lumen 12 can comprise other cross-sectional shapes that may call for various corresponding shapes of the flap member 24 and/or the fixation section 22. For example, the common lumen 12 could be provided with a rectangular cross-section which may call for a rectangular fixation section 22 and/or flap member outer surface 46.

The flap member 24 is sized and configured to resist being pushed into the main lumen 14 by back pressure in the common 12 or secondary 15 lumens. As used herein, the term "back pressure" refers to a fluid pressure in the common 12 or secondary 15 lumens that exceeds a fluid pressure in the main lumen 14. The check valve is preferably configured to resist back pressures at least as large as those expected in normal use, e.g., typically only a few inches of water. In some embodiments, a check valve can be configured to resist a back pressure of at least about 5 PSI (about 138.5" of $H_2O$). In other embodiments, a valve can be constructed to resist a back pressure as high as 35 PSI (i.e., a fluid pressure in the common 12 or secondary 15 lumens of about 35 PSI higher than a fluid pressure in the main lumen 14), or more.

The fixation section 22 can be secured within the common 12 or secondary 15 lumens of the Y-site 10 in any suitable manner. For example, in one embodiment, the fixation section 22 is press-fit into the common lumen 12 and is held in place simply by friction. In this embodiment, the fixation section can be provided with an outer diameter $D_o$ of between about 0.100" and about 0.140". Another preferred range is between about 0.110" and about 0.130", and in one preferred embodiment the outer diameter $D_o$ is about 0.120". The outer diameter $D_o$ is generally sized to correspond with an inner diameter of a lumen into which the fixation section 22 is intended to be fixed.

A fluorosilicone oil or other medically acceptable lubricant can be used to facilitate insertion of the check valve 20 into the common 12 or secondary 15 lumens of the Y-site. In alternative embodiments, the fixation section 22 can be glued, molded, welded or otherwise secured to the inner wall 34 (or other portion) of the Y-site common lumen 12.

The back-flow resistance function performed by the check valve 20 in the illustrated embodiments may be accomplished by a wide variety of other fluid-flow resistance structures such as gates, baffles, tortuous fluid pathways, expandable slits, and/or cuspid-type valves. The general positioning of the check valve 20, including the fixation section 22, can vary depending upon the chosen dimensions of the fixations section 22 and flap member 24 for a particular application, so long as the flap member 24 is configured to provide resistance to retrograde fluid flow into the hole 36. In some embodiments, the flap member 24 does not entirely seal of the hole 36, but merely provides sufficient resistance to diminish such flow.

Figure 8:
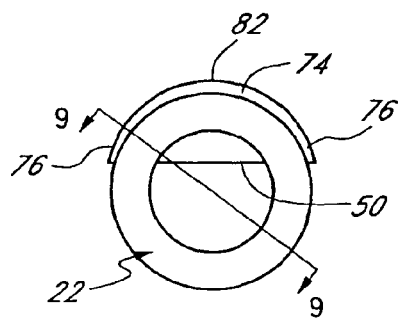
FIG. 8 is a proximal end view of the check valve of FIG. 6, taken at line 8-8.
Figure 9:
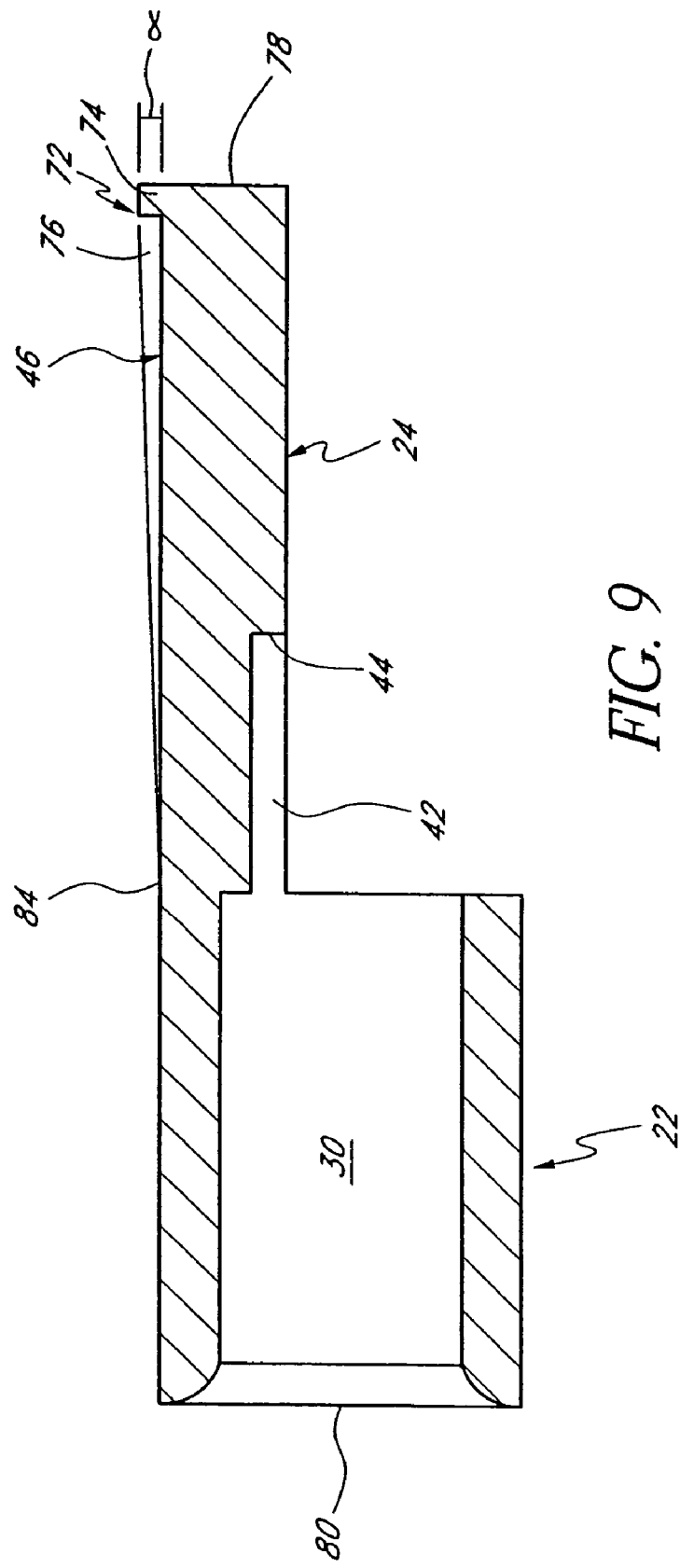
FIG. 9 is a cross-sectional view of the check valve of FIG. 8, taken at line 9-9.

The lumen 30 of the fixation section 22 can be substantially circular in cross-section (see, e.g., FIG. 8). The check valve lumen 30 can have any suitable internal diameter '$D_i$' that is sufficiently large to allow fluid to flow through the common 12 or secondary 15 lumens while preferably minimizing impedance to the flow through the respective lumens. For example, in some embodiments, the fixation section 22 has an inner diameter $D_i$ of between about 0.060" and about 0.100". In other embodiments, the inner diameter $D_i$ is between about 0.070" and about 0.090", and in one preferred embodiment the inner diameter $D_i$ is about 0.080". Additionally, in some embodiments, the fixation section 22 has a wall thickness $t_1$ of between about 0.010 and about 0.020, and one embodiment has a wall thickness $t_1$ of about 0.17". Some embodiments of a flap-type check valve 20 can have a fixation section 22 with a length $L_4$ of up to about half an inch. In other embodiments, the fixation section 22 has a length of between about 0.1" and about 0.3". One preferred embodiment of a fixation section has a length $L_4$ of about 0.250".

In the illustrated embodiment, the flap member 24 is resiliently biased towards the position shown in FIG. 1. In some embodiments, the check valve 20 is made of a material that is sufficiently resilient to produce bias in the flap member 24 toward a "closed" position, such as silicone rubber. In other embodiments, the flap member 24 can comprise a particular geometry or auxiliary mechanical biasing device (such as a spring or other elastic device) to provide the desired resilience to the flap member 24.

Figure 2B:
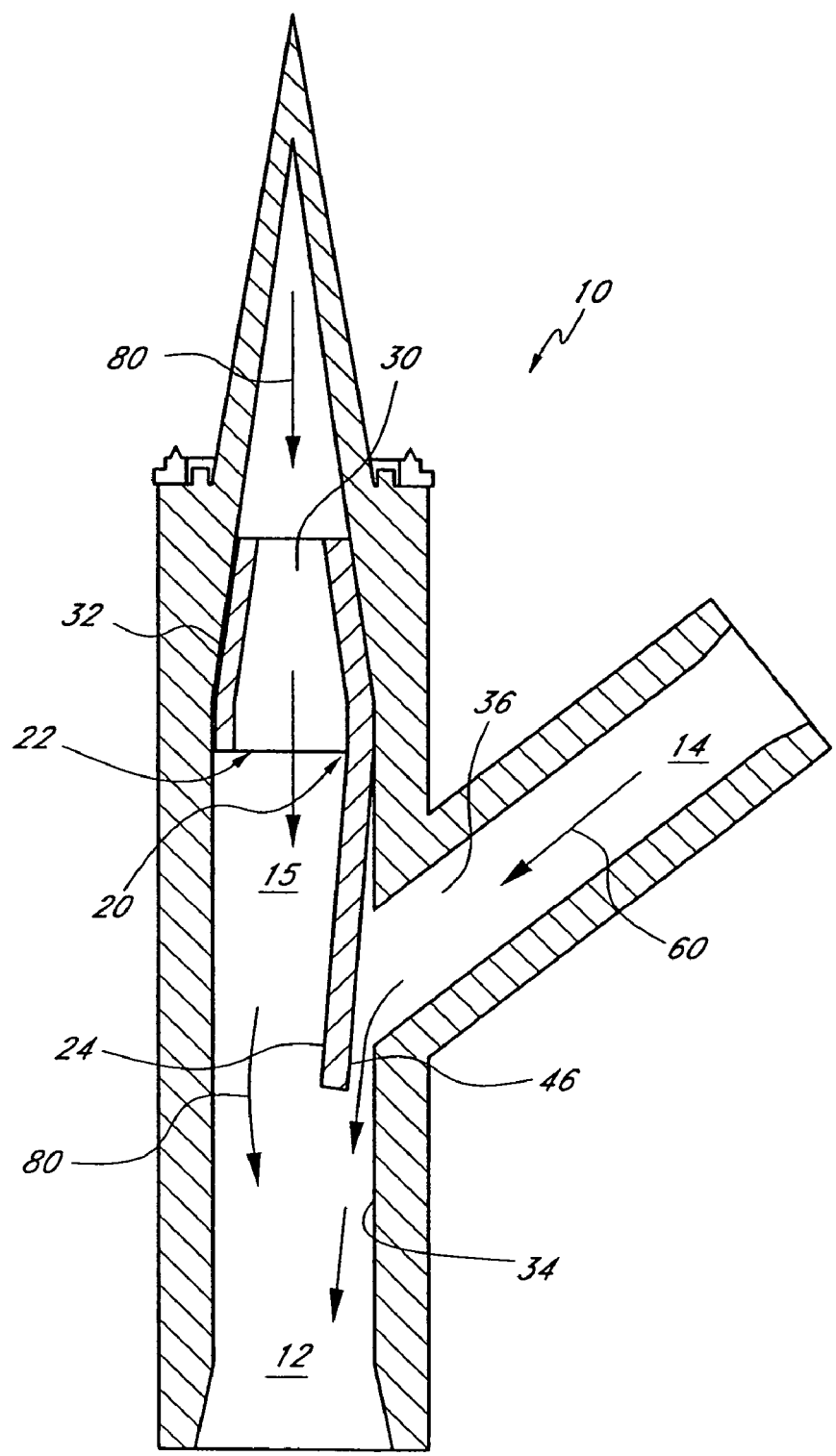
FIG. 2B is a schematic cross-sectional view of the Y-site of FIG. 1B with the check valve in an open position.

Referring to FIG. 2B, in the illustrated condition, the fluid pressure in the main lumen 14 is greater than the pressure of the fluid 80 in the common lumen 12. This pressure differential causes the flap member 24 of the check valve 20 to be displaced inwardly toward the longitudinal axis of the common lumen 12 and away from the common lumen inner wall 34 and the hole 36. In some embodiments, the flap member 24 resists opening against smaller pressure differentials until the magnitude of the pressure differential exceeds a certain threshold value.

The value of this threshold pressure can be selectively determined by varying design parameters of the check valve 20 and/or the Y-site 10. For example, a material or shape of the flap member 24 can be adjusted so as to increase or decrease the resilience, and thereby increase or decrease the closing force of the flap member 24 and the threshold pressure needed to open the valve in the forward flow direction. Additionally, in certain embodiments, the surfaces of the flap member 24 that are in contact with the surface of the common lumen inner wall 34 will tend to temporarily stick due to frictional, electrostatic or other forces, thereby causing a larger contact area to correlate with an increased threshold pressure differential needed to open the check valve. Thus, the threshold pressure differential can also be adjusted by increasing or decreasing a contact area between the flap member 24 and the common lumen inner wall 34. In some embodiments, it is desirable for the threshold pressure to be so small as to be substantially negligible. For example, the threshold pressure can be between about zero and about 9 inches of water (i.e., about 0.3 PSI). In other embodiments, the threshold pressure can be between about 4 and about 7 inches of water (i.e., about 0.14 PSI to about 0.25 PSI). In one preferred embodiment, the threshold pressure is no greater than about 6 inches of water (about 0.22 PSI).

The flap member 24 can be integrally molded with the fixation section 22 in order to provide a unitary check valve. Alternatively, the flap member 24 and the fixation section can be fabricated separately and subsequently joined together by adhesives, welds, or other joining means. The check valve 20 can be molded, extruded, or cast from a variety of appropriate materials, such as silicone rubber, elastomeric polymers or other medically-acceptable materials. If extruded, the check valve can be cut or modified in some other way to create a flap member and a fixation section. The Y-site can also be made as a unitary structure with an appropriately configured check valve structure, potentially simplifying the manufacturing and assembly processes.

In one embodiment, the check valve 20, including the fixation section 22 and the flap member 24, is molded from a silicone rubber material. The check valve can be made from any suitable medically acceptable material. In some embodiments, the flap member 24 has a length $L_3$ of between about 0.1" and about 0.5". In other embodiments, the flap member 24 has a length $L_3$ of between about 0.2" and about 0.4", and in one particular embodiment, the flap member 24 has a length $L_3$ of about 0.35".

The resilience of the flap member 24 can be at least partially determined by the thickness of the flexing portions of the flap member 24. In some embodiments, the proximal section 52 of the flap member 24 has a thickness $t_1$ of between about 0.010" and about 0.040", and in one preferred embodiment a thickness $t_1$ about 0.017". In some embodiments, the distal section 54 of the flap member 24 has a thickness $t_2$ of between about 0.010" and about 0.050", and in one preferred embodiment the flap has a thickness $t_2$ of about 0.037". Of course, dimensions within and outside of these ranges can also be used as appropriate for any particular application.

Figure 3:
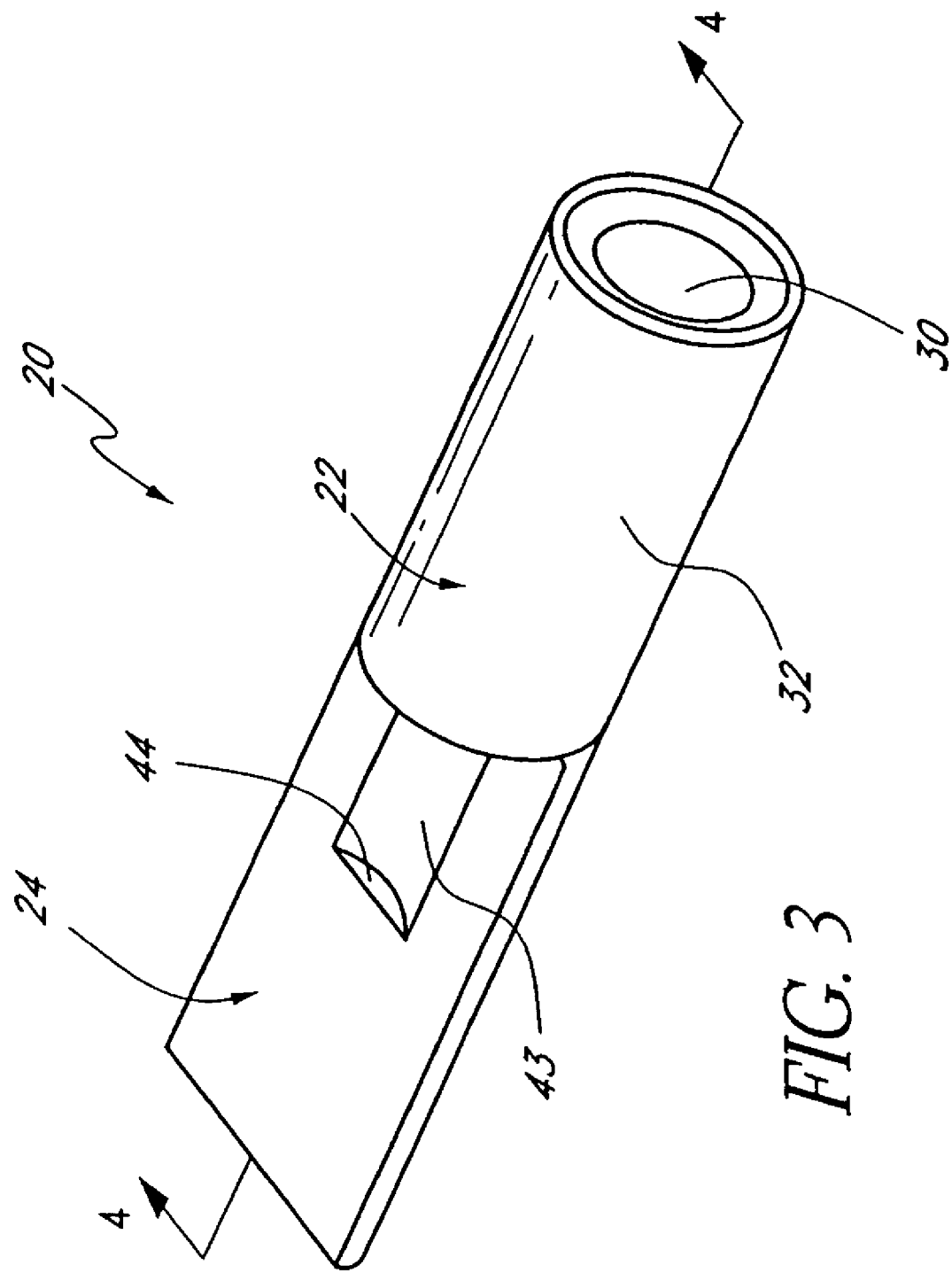
FIG. 3 is a perspective view of an embodiment of the check valve of FIGS. 1B-2B.
Figure 4:
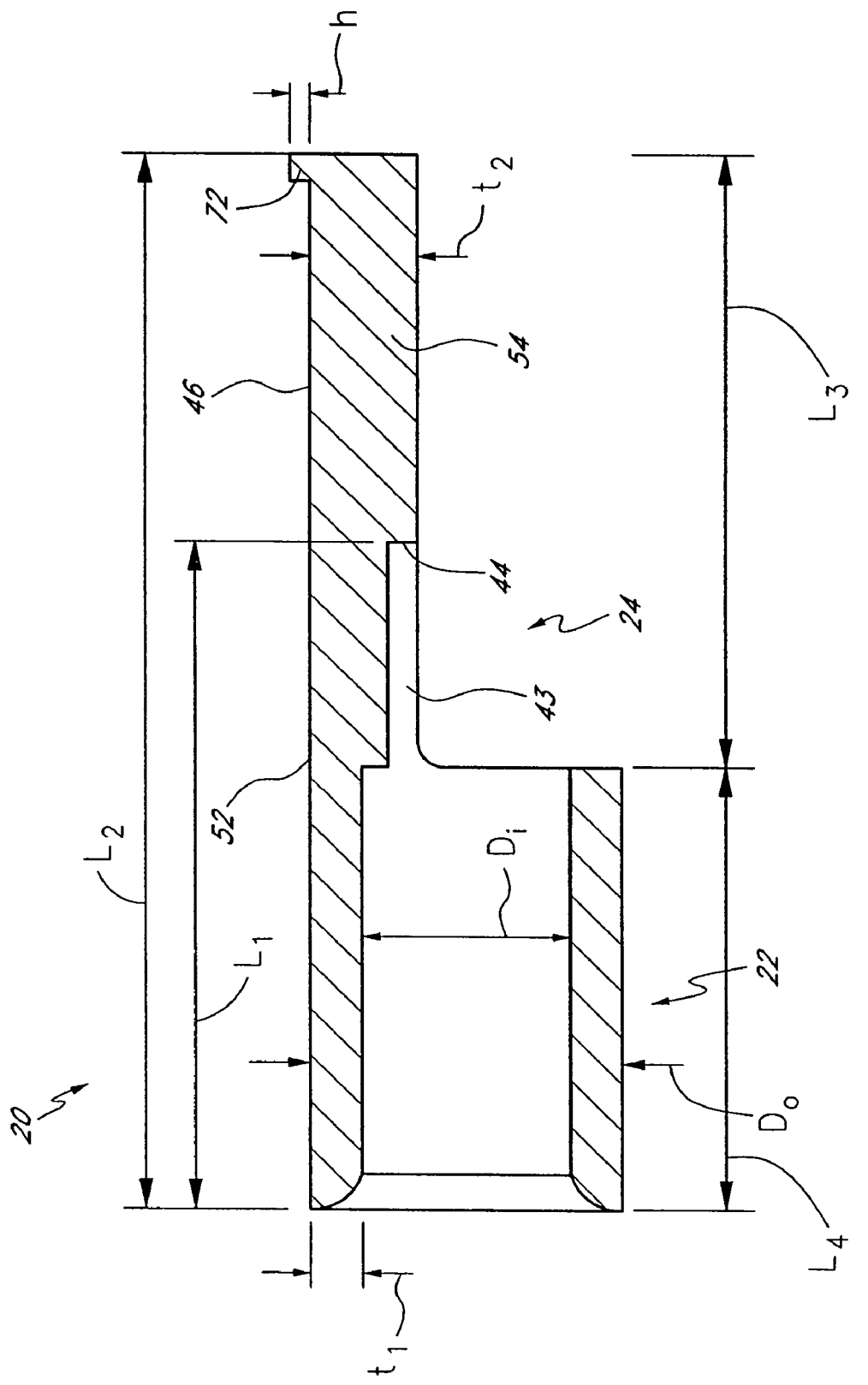
FIG. 4 is a cross-sectional view of the check valve of FIG. 3, taken at line 4-4.

In some embodiments, as illustrated for example in FIGS. 3 and 4, a portion of the flap member 24 can include a cutout 43. In one embodiment, the cutout 43 continues the profile of the check valve lumen 30 for a portion of the length of the flap member 24. If the cutout 42 is omitted, the proximal 52 and distal 54 sections of the flap member 24 can have approximately the same thickness. In the embodiments shown in FIGS. 3 and 4, the cutout 43 comprises a shoulder 44 at a distal end thereof. In some embodiments, the length $L_1$ of the lumen 30 including the cutout 43 is between about 0.2" and about 0.6", and in other embodiments is between about 0.3 and about 0.5". In one embodiment, the length $L_1$ is about 0.4". In further alternative embodiments, other dimensions can be used as appropriate. In alternative embodiments, the cutout 43 can comprise a tapered distal end 44, or the cutout 43 can continue for the entire length of the flap member 24. The check valve lumen 30 need not have a circular cross-section; for example, the cross-section can also be rectangular, elliptical, polygonal, or D-shaped.

Y-sites are typically injection molded from medical grade plastics. As an artifact of the manufacturing process, injection molding often leaves flash (not shown) in the form of raised burrs or other excess material. The flash is often parallel to the main lumen wall 28 and extends into the common 12 and/or secondary 15 lumens surrounding the hole 36. In some instances, the flash can interfere with the functioning of a check valve having a flap member as described above by potentially preventing the outer surface 46 of the flap member 24 from sealing against the inner wall 34 of the common lumen 12. One way to circumvent this is to remove the flash, such as by grinding, filing or some other post-production method. However, such processes can be labor intensive, inefficient and costly. Thus, a preferred alternative involves providing a flap member 24 of the check valve 20 configured to accommodate the flash and to function as described above despite the presence of flash on the common lumen wall surrounding the intersection hole 36.

FIGS. 5-13 illustrate some embodiments of a check valve 20 configured to seal an injection lumen 14 from back-flow while avoiding flash surrounding the intersection hole 36 and requiring a minimal threshold injection pressure. In the illustrated embodiments, these advantages are generally be achieved by providing an enclosed pocket 70 in the outer surface 46 of the flap member 24. Such a pocket 70 can allow a flash or burr material to extend into a space created by the pocket while the walls surrounding the pocket seal against the lumen wall. In some embodiments, such a pocket 70 can be formed by a flange 72 surrounding the perimeter of the outer surface 46 of the flap member 24.

Figure 5:
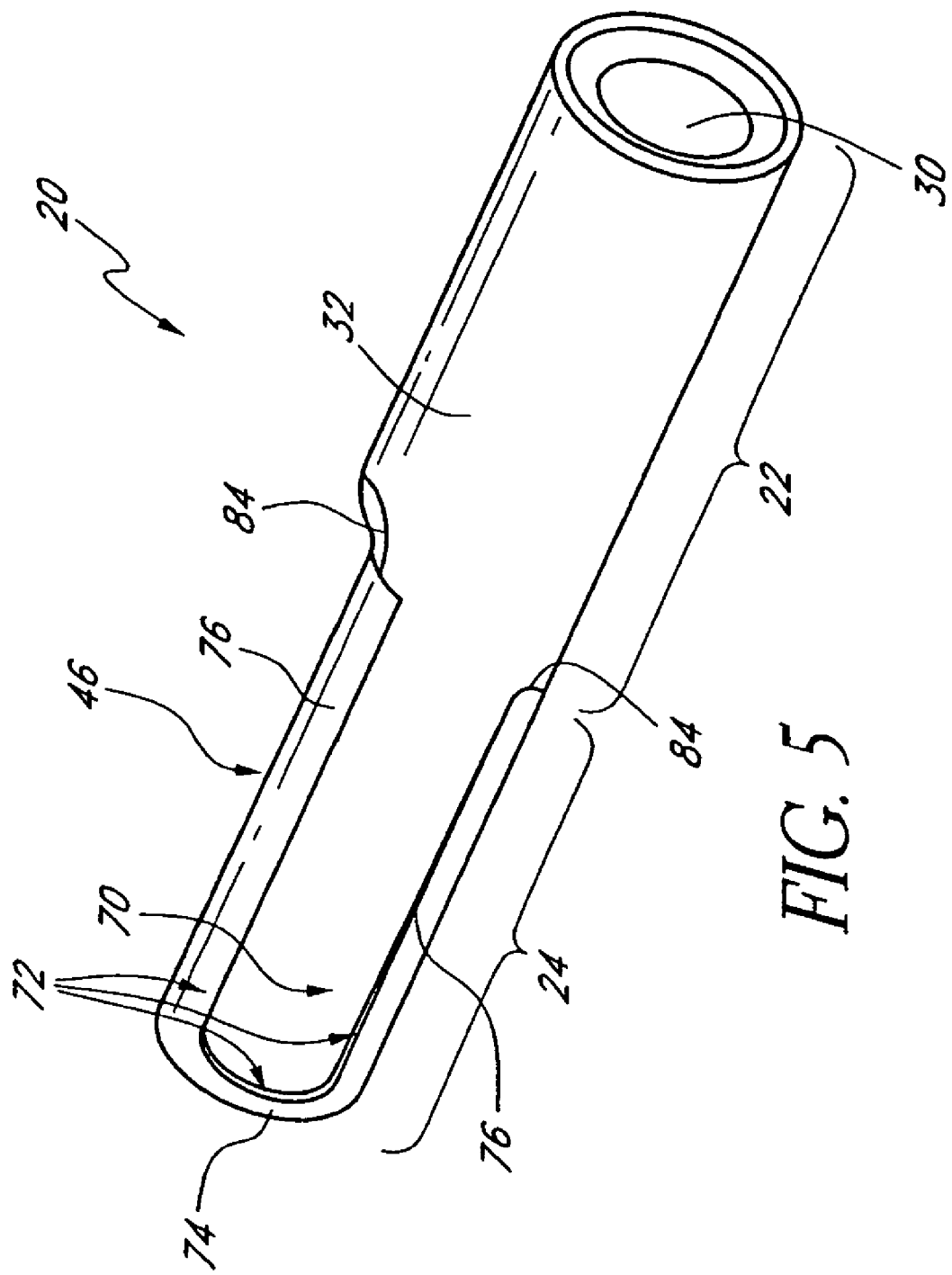
FIG. 5 is a perspective view of a check valve having a flange on a flap portion.
Figure 6:
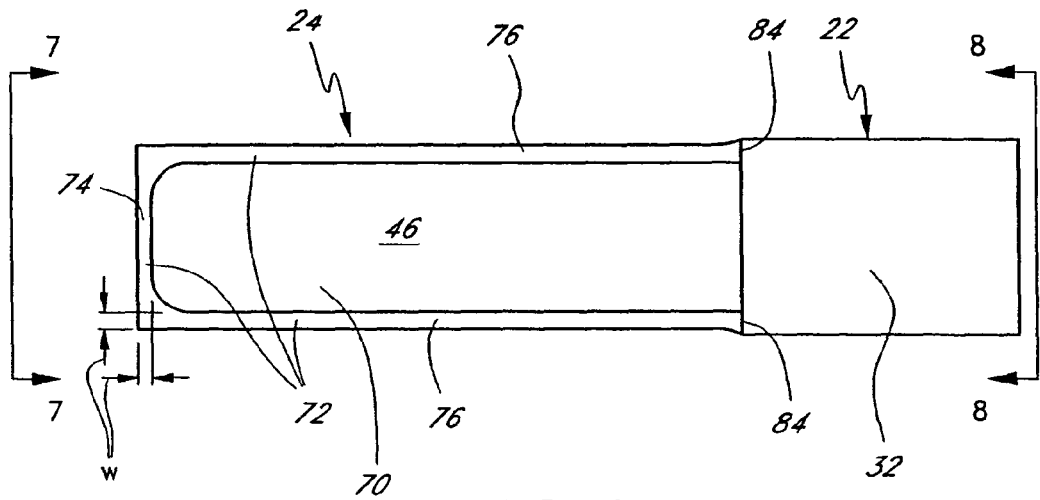
FIG. 6 is a plan view of the check valve of FIG. 5.

FIG. 5 illustrates an embodiment of a check valve 20 having a cylindrical fixation section 22 with a hollow lumen 30 and a flap member 24 extending in a distal direction from the fixation section 22. The flap member 24 comprises a flange 72 extending outward from portions of the flap member 24. In the illustrated embodiment, the flange 72 generally comprises an end portion 74 and first and second flange legs 76 extending along the long edges of the flap member 24. In the illustrated embodiment, the flange 72 is relatively narrow and surrounds a periphery of the flap member outer surface 46. In one embodiment, as illustrated in FIG. 6, the flange 72 has a width 'w' of about 0.005". In some embodiments, the flange 72 is about 0.010" wide. In other embodiments, the flange 72 can extend over smaller or larger portions of the flap member 24 as desired.

In some embodiments, a pocket 70 is formed by a flange 72 surrounding a central portion of the outer surface 46 of the flap member 24. This pocket 70 is generally sized to enclose any flash extending into the common lumen of the Y-connector around the hole 36 so that the flange 72 can seal against the common lumen inner wall 34. The flange 72 also creates a small contact area between the flap member 24 and the inner wall 34 of the common lumen 12. As discussed above, such a reduction in sealing area can result in an advantageous reduction in threshold pressure needed for fluid to flow from the main lumen 14 into the common lumen 12.

Figure 7:
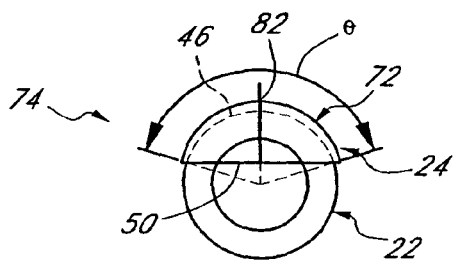
FIG. 7 is a distal end view of the check valve of FIG. 6, taken at line 7-7.

In one embodiment, as shown in FIG. 7, the flange 72 comprises an arcuate end section 74 extending outwards from the distal end 78 of the flap member 24. The arcuate end section 74 of the flange 72 can have substantially the same radius as the outer surface 46 of the flap member 24, and a center that is preferably shifted radially from the center of the circular fixation section 22 and the flap member outer surface 40. The radius of the arcuate section 74 of the flange 72 can be selected to correspond to a diameter of the inner wall of a Y-site common lumen.

In the embodiments illustrated in FIGS. 7 and 8, the flap member 24 comprises a substantially D-shaped cross section. The flat edge 50 of the flap member 24 forms a geometric chord which subtends an arc θ of less than 180° measured from the center of the circular fixation section 22. In this example, the chord 50 subtends an arc θ of between about 90° and about 180°, and in one preferred embodiment, the chord 50 preferably subtends an arc θ of about 135°. Alternatively, the chord 50 could be configured to subtend an arc of less than 90° as appropriate for any particular application.

In one embodiment, as illustrated in FIGS. 7 and 8, the flange 72 can be configured to taper from a high point 84 at a center of the arcuate end section 74 to a pair of low points 84 at the intersection of the flap member 24 with the fixation section 22. At the high point 84, the flange 72 can extend about 0.005" to about 0.030" above the flap member 24 outer surface 46. In one embodiment, the high point is about 0.010" above the flap member 24 outer surface 46, and the angle α at which the flange 72 tapers can be between about 1° and about 2° (see FIG. 9). In one preferred embodiment, the taper angle is about 1.6°. In alternative embodiments, a flange can be provided with a greater or lesser length or angle of taper as desired. For example, the low points 84 of the flange legs 76 could alternatively be located at other points along the flap member. The flange could also extend the entire length of the check valve to the proximal end 80 of the fixation section.

In one embodiment, the low points 84 of the flange 72 are substantially continuous with the outer surface 32 of the fixation section 22. Alternatively, the valve 20 can comprise a discontinuity such as a ledge or a groove at or near the intersection of the flange 72 with the fixation section 22 in order to allow for variation in the seal between the valve 20 and the internal common lumen wall 34.

The pocket 70 can be formed in a flap member 24 by any suitable means. For example, in some embodiments such as those discussed above, a flange 72 can be molded as a unitary structure with the flap member 24 and/or the fixation section 22.

In one embodiment, a check valve according to some of the embodiments described above allows fluid to flow from the main lumen to the common lumen at a rate of about 330 cc/min at a pressure of 36 inches of water (about 1.3 PSI). In still further embodiments, rates within or outside of the ranges disclosed herein can also be achieved.

Figure 10:
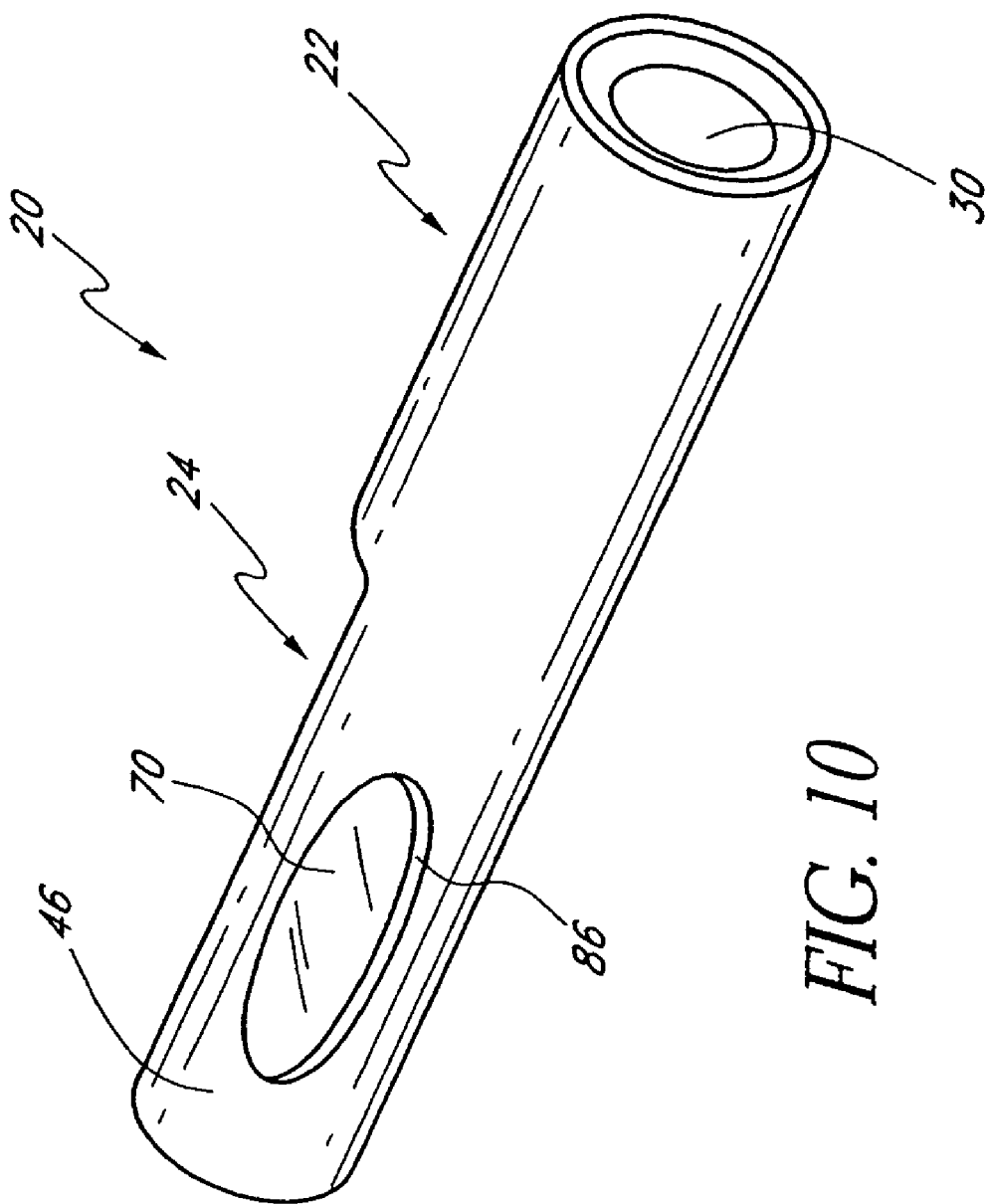
FIG. 10 is a perspective view of an alternative embodiment of a check valve.

In alternative embodiments, illustrated for example in FIG. 10, a pocket 70 can be formed by cutting out a section of the flap member 24, or by molding a depression into the outer surface 46 of the flap member 24. Additionally, a depression or flange can be formed so as to create a pocket 70 with linear, arcuate, rounded, serpentine, or otherwise shaped side walls 86 surrounding the pocket 70.

Figure 11:
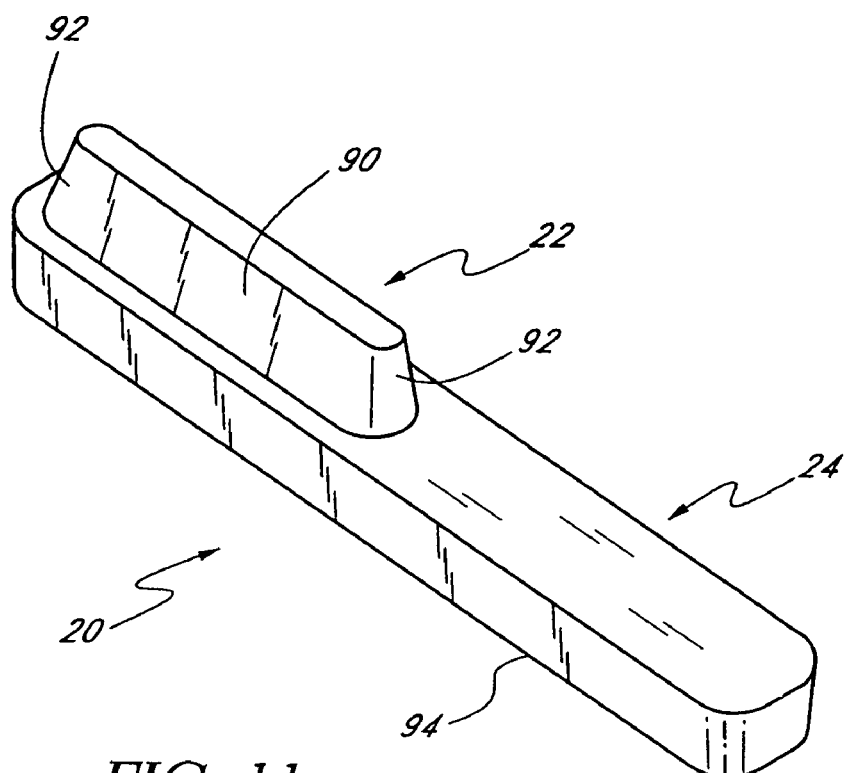
FIG. 11 is a perspective view of another alternative embodiment of a check valve.
Figure 12:
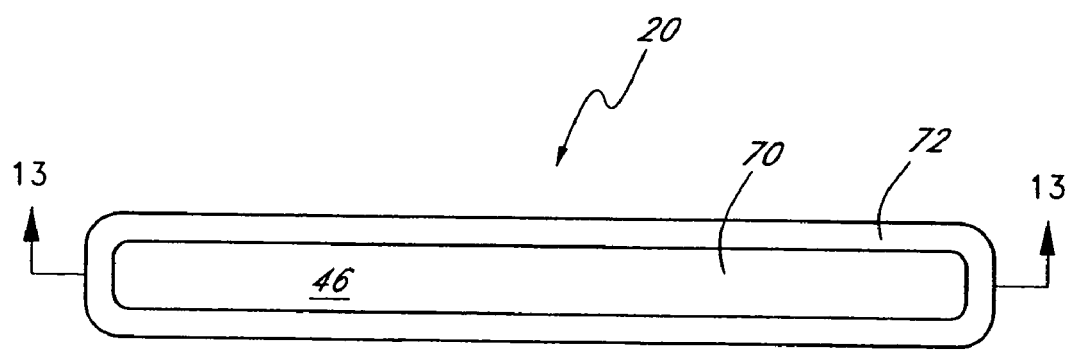
FIG. 12 is a plan view of the check valve of FIG. 11.
Figure 13:
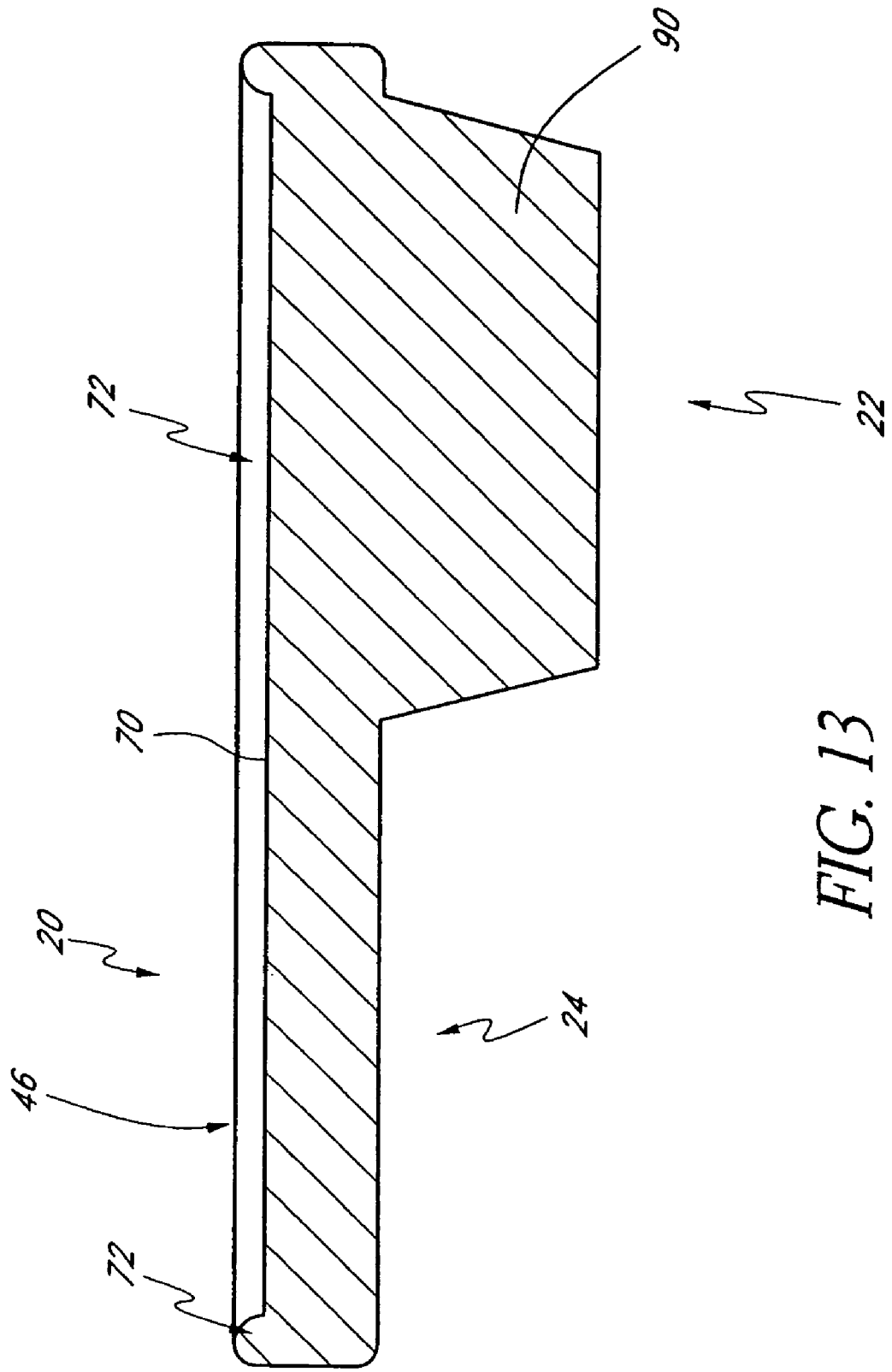
FIG. 13 is a side plan view of the check valve of FIG. 12, taken at line 13-13.

FIGS. 11-13 illustrate another embodiment of a check valve 20 for use in preventing unwanted fluid flow in a Y-site. According to this embodiment, the fixation section 22 can comprise a protrusion, such as a prismatic body 90, configured to retain the check valve 20 in a Y-site common lumen while allowing fluid flow around the protrusion. In the illustrated embodiment, the protrusion is a prismatic body 90 that is substantially trapezoidal in cross-section (both axial and transverse). The illustrated prismatic body 90 also comprises rounded portions 92 at leading and trailing ends in order to improve fluid flow around the body 90. In alternative embodiments, the protrusion of the fixation section 22 can comprise a solid or hollow section having any suitable cross-sectional shape configured to allow fluid flow around or through any portion thereof.

The embodiment of FIGS. 11-13 can include a substantially flat outer surface 46 with a flange 72 extending substantially around the entire periphery of the valve 20. Thus, the pocket 70 can extend substantially along the entire length of the flap member 24 and the fixation section 22. If desired the edge regions 94 of the valve 20 can have a radius configured to improve a seal between the valve 20 and the inner wall of a Y-site.

Figure 14:
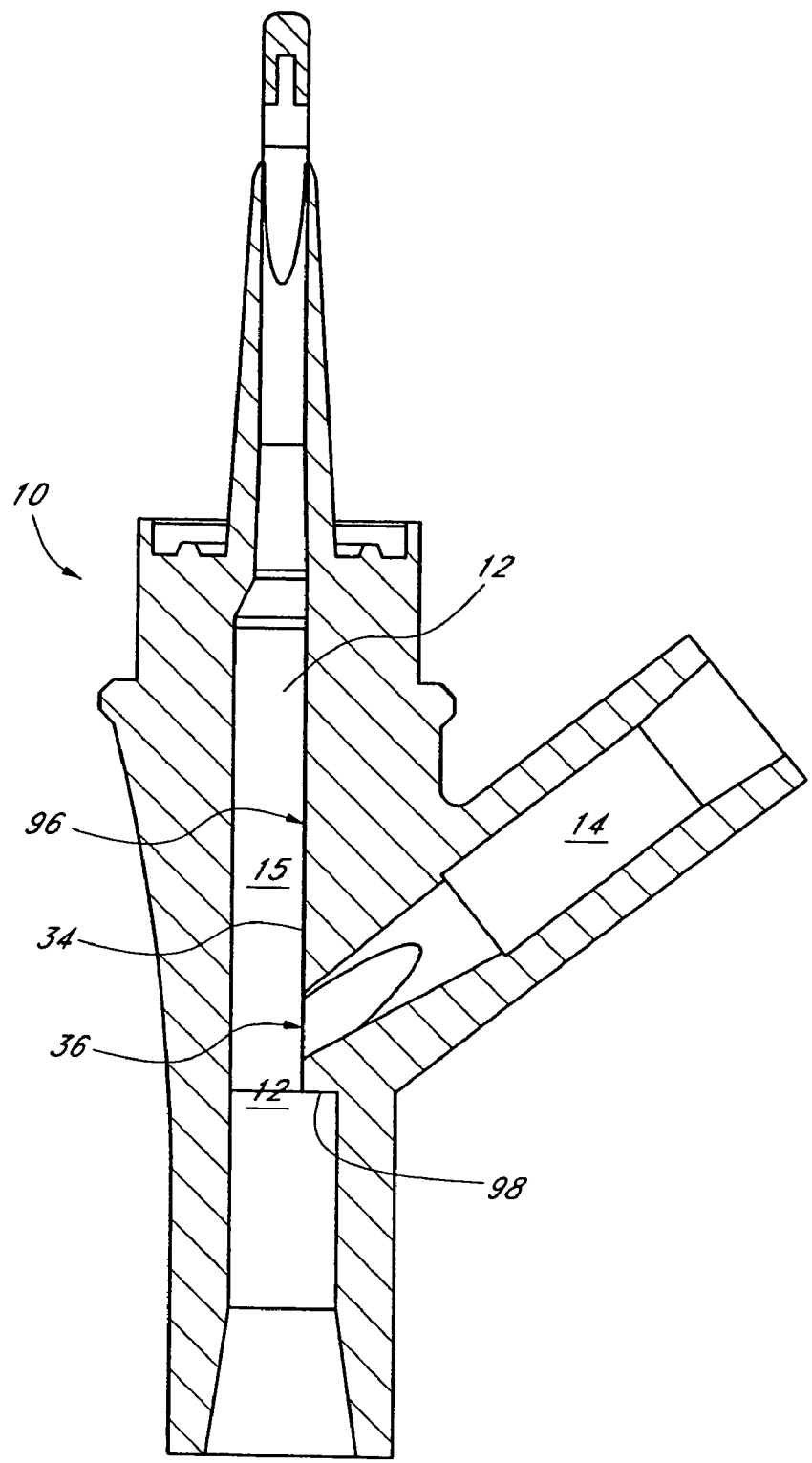
FIG. 14 is a cross-sectional view of a Y-site that is especially, though no exclusively, appropriate for use with the check valves disclosed herein.

In some embodiments, as shown for example in FIG. 14, a Y-site 10 can be molded with a planar section 96 adjacent the main lumen 14 and configured to receive a check valve 20 with a planar outer surface 46 such as that illustrated and described herein. The Y-site of FIG. 14 is also shown with a step 98 at a point of increasing diameter just below the hole 36 joining the main lumen 14 to the common lumen 12. This configuration further decreases the likelihood that fluid at a level below the hole 36 will be forced upwardly by retrograde fluid pressures through the hole 36 and into the main lumen 14 because such upwardly directed fluid would first encounter the step 98 instead of the flap member 24 of the check valve 20.

Although certain embodiments and examples have been described herein, it will be understood by those skilled in the art that many aspects of the methods and devices shown and described in the present disclosure may be differently combined and/or modified to form still further embodiments in view of the principles disclosed herein. For example, other flap member arrangements can also be provided, such as a slit or a port in a section of tubing. Also, as discussed above, the flap member and the fixation section can have any suitable cross-sectional shape as desired. Although the above check valve embodiments have been described in the context of a Y-site connector, they can also be used in other fluid conduits with intersecting fluid lumens.

The following is claimed:

1. A connector comprising:
   a lumen extending in a first direction, the lumen having a hole in a wall of the lumen;
   a check valve comprising:
      a first end defining a fixation portion configured to frictionally retain the check valve within the lumen, the fixation portion having an inner surface;
      a prismatic protrusion extending from the inner surface of the fixation portion in a second direction, the protrusion and the fixation portion being configured to retain the check valve within the lumen, the protrusion configured to allow fluid flow around a portion thereof;
      a second end including a flap member extending from the fixation portion in the first direction, the flap member having an outer surface configured to at least partially overlay the hole in the lumen, the flap member being configured to at least partially impede a flow of fluid through the hole the flap member bein further configured to flex in the second direction and away from the hole;
      a pocket in a portion of the flap member, the pocket being defined by a flange raised with respect to an inner surface of the pocket to create a space, the flange being configured to surround the hole in the lumen;
   wherein the flap member is resiliently biased in the second direction.

2. The connector of claim 1, wherein the flange extends along the outer periphery of the outer surface of the flap member.

3. The connector of claim 1, wherein the flange extends substantially around the entire periphery of an outer surface of the check valve.

4. The connector of claim 3, wherein the pocket extends substantially along the entire length of the flap member and the fixation portion.

5. The connector of claim 1, wherein the first and second directions are perpendicular to one another.

6. The connector of claim 1, wherein the check valve is a single unitary structure molded from a flexible material.

7. The connector of claim 1, wherein at least the flap member is molded from silicone rubber.

8. The connector of claim 1, wherein the flap member further comprises a cut-out on the surface to facilitate flexing of the flap member.

9. The connector of claim 1, wherein the connector is a Y-site.

* * * * *

UNITED STATES PATENT AND TRADEMARK OFFICE
CERTIFICATE OF CORRECTION

PATENT NO. : 7,931,627 B2  
APPLICATION NO. : 11/415995  
DATED : April 26, 2011  
INVENTOR(S) : Thomas F. Fangrow, Jr.

Page 1 of 1

It is certified that error appears in the above-identified patent and that said Letters Patent is hereby corrected as shown below:

On the Title Page (Item 57), line 8, after "surrounds" please delete "surrounding".

At Page 2 (Item 56), line 49, under U.S. Patent Documents, please change "11/2005" to --12/2005--.

At Page 2 (Item 56), line 71, under Other Publications, please change "2008" to --2006,--.

At Column 10, line 5, in Claim 1, please change "hole" to --hole,--.

At Column 10, line 5, in Claim 1, please change "bein" to --being--.

Signed and Sealed this  
Eleventh Day of October, 2011

David J. Kappos  
*Director of the United States Patent and Trademark Office*